United States Patent [19]

Nelles

[11] Patent Number: 4,777,242

[45] Date of Patent: Oct. 11, 1988

[54] PURIFICATION OF RECOMBINANT TUMOR NECROSIS FACTOR

[75] Inventor: Lynn P. Nelles, Bartlesville, Okla.

[73] Assignee: Phillips Petroleum Company, Bartlesville, Okla.

[21] Appl. No.: 917,625

[22] Filed: Oct. 10, 1986

[51] Int. Cl.$^4$ ............................................. C07K 3/28
[52] U.S. Cl. ..................... 530/351; 530/412; 530/415; 530/416; 530/417; 530/820; 435/68; 435/70; 435/803
[58] Field of Search ..................... 530/412, 415–417, 530/351, 820, ; 435/68, 70, 803

[56] References Cited

U.S. PATENT DOCUMENTS

| | | | |
|---|---|---|---|
| 4,495,282 | 1/1985 | Ohnishi et al. | 435/68 |
| 4,518,584 | 5/1985 | Mark et al. | 424/85 |
| 4,530,787 | 7/1985 | Shaked et al. | 260/112 |
| 4,588,585 | 5/1986 | Mark et al. | 424/85 |
| 4,677,197 | 6/1987 | Lin | 530/351 |

FOREIGN PATENT DOCUMENTS 0090892 10/1983 European Pat. Off. .

OTHER PUBLICATIONS

Matthews, B I Cancer 40, 1979, pp. 534–539.
Sofer, Bio Technology 4, 1986, pp. 712–715.
Ruff et al, Lymphopine vol. 2, 1981, p. 235 (partial copy).
Dean et al, I Chromat 165, 1979, pp. 301–319.
Bonneyea et al, Bio Technology 4, 1986, pp. 954–958.
"Designing an Optimal Chromatographic Purification Scheme for Proteins", G. Sofer and V. J. Britton, BioTechniques, pp. 198–203 (Nov./Dec., 1983).
Purification and Characterization of a Human Tumor Necrosis Factor from LuKII Cell Line", B. Y. Rubin, et al, Proc. Natl. Acad. Sci. USA, vol. 82, pp. 6637–6641 (10/85).
"Human Tumor Necrosis Factor", B. B. Aggarwal, Journal of Biological Chemistry, vol. 260, pp. 2345–2354 (1985).
"Dye-Ligand Chromatography" product brochure from Amicon, pp. 2–4, 6–10, 12, 20–26 and 30–33.

Primary Examiner—J. R. Brown
Assistant Examiner—Garnette D. Draper
Attorney, Agent, or Firm—J. E. Phillips

[57] ABSTRACT

A method for purifying recombinant tumor necrosis factor from cultures of microorganisms transformed with vectors that code for the production of tumor necrosis factor is disclosed. A sequence of contacting steps is involved, such that the effluent from the first contacting step can be contacted directly with the contacting material used for the second step and similarly, the effluent from the second contacting step can be contacted directly with the contacting material used for the third contacting step. In a preferred embodiment, tumor necrosis factor-containing fermentation broth can be substantially purified by a single pass through a multi-component chromatography system, i.e., the first, second and third contacting materials are each packed in a column configuration, with TNF-containing broth being passed directly through the sequence of columns. The need for intermediate isolation, concentration, reconstitution, and the like of the tumor necrosis factor-containing fractions is therefore avoided by the practice of the present invention.

16 Claims, No Drawings

PURIFICATION OF RECOMBINANT TUMOR NECROSIS FACTOR

This invention relates to the isolation and purification of tumor necrosis factor (TNF) produced by genetically modified microorganisms.

BACKGROUND

As recombinant DNA technology has developed in recent years, the controlled production by microorganisms of an enormous variety of useful polypeptides has become possible. Many eukaryotic polypeptides, such as for example, human growth hormone, leukocyte interferons, human insulin and human proinsulin have already been produced by microorganisms. The continued application of techniques already in hand is expected in the future to permit production by microorganisms of a variety of other useful polypeptide products. One such useful polypeptide product is human tumor necrosis factor.

Tumor necrosis factor (TNF) is an antitumor substance found in the sera of animals that have been treated with microbial products in two orderly events. The first event is a priming event that causes the activation and proliferation of macrophages and is associated with expansion of reticuloendothelial elements in the liver and spleen. For this priming event, micobacteria such as Bacilus Calmette Guerin (BCG), corynbacteria such as *Cornynebacterium parvum* and zymosan (yeast cell walls) are effective. The second event is an elicitation event which is necessary for the apperance of TNF in the blood. This requires subsequent treatment of primed animals with lipopolysaccharide (LPS—a major constituent of the cell wall of gram-negative bacteria, also known as endotoxin or bacterial pyrogen). Using these principles, one can obtain sera with similar antitumor and cytotoxic properties from mice, rats and rabbits.

The cellular origin of TNF is macrophages (monocytes), thus, TNF is also referred to as a monokine. TNF causes haemorrhagic necrosis and sometimes complete regression of certain tumors transplanted in mice and shows cytotoxic activity against certain tumor cell lines, but not against normal cells.

Recombinant DNA techniques by which DNA that codes for peptides having TNF activity is introduced into a cell to express TNF or TNF analogs is believed to represent the best hope of inexpensively producing large quantities of TNF. By transforming appropriate host organisms with DNA which encodes the TNF amino acid sequence, genetically modified microorganisms can be employed to product TNF in significant quantities. One barrier to employing recombinant DNA technology for the commercial production of TNF is the need to be able to rapidly and efficiently recover TNF in biologically active form from genetically modified microorganisms which product the desired TNF.

OBJECTS OF THE INVENTION

An object of the present invention, therefore, is to provide a method for the efficient recovery of biologically active TNF produced by genetically modified microorganisms.

This and other objects of the present invention will become apparent from inspection of the disclosure and claims herein provided.

STATEMENT OF THE INVENTION

In accordance with the present invention, I have developed a method for the isolation and purification of tumor necrosis factor produced by genetically engineered microorganisms. The invention method is particularly useful for the recovery of TNF produced by recombinant yeast strains. The method which I have developed involves the use of three separate, yet coordinated contacting steps carried out in a specified sequence so that the effluent from the first contacting step can be employed directly as the feed for the second contacting step, and the effluent from the second contacting step can be employed directly as the feed for the third contacting step.

By the practice of the present invention, production of highly purified recombinant TNF is made possible without the need for sample concentration and re-formulation during the sequence of contacting steps. As a result of the invention simplified purification process, a number of advantages are realized, e.g., handling losses of the desired recombinant product are minimized; a lesser quantity of reagents are required for sample purification; a reduced volume of waste streams is generated; and sample degradation during the purification is minimized due to the reduced amount of sample manipulation required for TNF purification.

DETAILED DESCRIPTION OF THE INVENTION

In accordance with the present invention, I have developed a method for the isolation and purification of tumor necrosis factor (TNF) produced by genetically modified microorganisms which method comprises:

(a) applying disrupted, clarified fermentation broth containing TNF to a high surface area, porous glass material;

(b) washing the high surface area, porous glass material loaded in accordance with step (a) with a suitable buffer;

(c) eluting a first TNF-containing fraction from the high surface area, porous glass material washed in accordance with step (b) with a solution comprising in the range of about 0.01 up to 10 V/V% of a suitable eluant;

(d) contacting the first TNF-containing fraction obtained from step (c) with an anion exchange resin;

(e) eluting a second TNF-containing fraction from said anion exchange resin with a solution comprising salt in a buffer, wherein the salt concentration and pH of said solution are sufficient to cause elution of the second TNF-containing fraction from said anion exchange resin but insufficient to prevent binding of the TNF in the second TNF-containing fraction to the dye affinity material employed in step (f);

(f) contacting the second TNF-containing fraction from said anion exchange resin with an immobilized dye affinity material;

(g) washing the TNF-containing immobilized dye affinity material prepared in accordance with step (f) with a suitable buffer until essentially no material with a uv absorbance of about 280 nm is eluted, and (h) eluting purified TNF from the washed, TNF-containing immobilized dye affinity material with an eluant comprising a sufficient concentration of salt in a buffer with a pH in the range of 6.5 up to 10 to cause desorption of the TNF from said dye affinity material without causing degradation of the TNF.

All of the above-described manipulations are typically carried out at about 4° C. to minimize the occurrence of proteolytic degradation and to minimize thermal inactivation of the TNF. I have found that the above-described manipulations can be carried out at a variety of temperatures in the range of about 4° up to 25° C.

In a preferred embodiment of the present invention, each of the solid contacting materials employed, i.e., the high surface area, porous glass material, the anion exchange resin, and the immobilized dye affinity material, are contained in a packed column configuration. Such a configuration enables the TNF-containing solutions, and the additional treating solutions to which the solid contacting materials are subjected, to simply be allowed to pass through a packed column of the appropriate solid contacting material. Moreover, operation of the present invention is this packed column mode allows the direct passage of the effluent from the high surface area, porous glass material-packed column to the anion exchange resin-packed column, as well as the direct passage of the effluent from the anion exchange resin-packed column to the immobilized dye affinity material packed column. Thus, the column configuration provides an extremely efficient means for the practice of the present invention.

As employed in this specification, the term "tumor necrosis factor" is intended to encompass all proteins, both naturally occurring and synthetic, which possess the anti-tumor properties observed of naturally occurring tumor necrosis factor $\alpha$ (TNF$\alpha$, generally referred to in this specification simply as "TNF") molecules. Thus, TNF from a variety of natural sources as well as analogs and derivatives thereof are contemplated to be within the scope of the present invention.

The present invention involves the isolation and purification of tumor necrosis factor (TNF) produced by a genetically modified microorganism. Any microorganism capable of producing heterologous protein products is useful in the practice of the present invention. Presently preferred are yeast strains because of their proven ability to express heterologous proteins at high levels and in biologically active form. Particularly preferred are strains of *Pichia pastoris* and *Saccharomyces cerevisiae* because of their established ability to produce high levels of biologically active recombinant proteins.

The producton of TNF to very high levels in *Pichia pastoris* is described by Streekrishna, Fuke and Potenz in copending applicaton Ser. No. 909,528 filed Sept. 22, 1986, to which the reader is directed for greater detail on the recombinant production of TNF, and which disclosure is hereby incorporated by reference herein.

The first step in the inventive purification process is to apply disrupted, clarified, fermentation broth to a high surface area, porous glass material. As noted above, in a preferred embodiment of the present invention, this high surface area, porous glass material will be employed in a column configuration. For convenience, the high surface area, porous glass material contained in a column is sometimes referred to as the "first column", since this is the material used in the first contacting step of my integrated multiple contacting procedure for the purification of TNF.

The column packing employed in this first column is composed of porous granules of high silica glass permeated by interconnecting pores of uniform and precisely controlled size. Pore sizes in the range of about 300 up to 3000 Angstroms (expressed as mean pore diameter) are suitable for use in the practice of the present invention, with pore sizes in the range of about 500 up to 1000 Angstroms preferred. In addition to the uniform pore size, the packing material employed in the first column has the same pore size near the surface as in the interior. Thus, mesh size of the packing material employed is relatively unimportant, and can vary between wide limits. Those of skill in the art recognize that large particles will typically allow for faster flow of material through the column, while smaller particles will typically allow for more efficient column packing (i.e., less void space). The surface area of the first contacting material can vary between wide limits, and will vary as a function of the mean pore diameter of the particles employed. Typically, the materials employed in this first contacting step will have a surface area in the range of about 10 up to 100 $m^2/g$, with surface areas in the range of about 20 up to 50 $m^2/g$ being preferred.

Prior to loading this first column with the TNF-containing broth, the column is typically equilibrated employing techniques known by those of skill in the art. Any buffer capable of maintaining a pH in the range of about 6.5 up to 7.5 or so is suitable for carrying out such equilibration. Buffers having a concentration in the range of about 0.002 up to 0.1M are suitable. Higher buffere concentrations should be avoided as they tend to suppress elution of contaminant proteins. In practice, I prefer to use phosphate buffers, with an exemplary buffer comprising 0.01M potassium phosphate having a pH of about 7.5.

The amount of TNF-containing fermentation broth which is contacted with the high surface area, porous glass material can vary within wide limits. The appropriate loading level will vary as a function of the TNF concentration in the broth, the substrate on which the TNF-producing microorganisms were grown, the concentration of other proteins and soluble non-proteinaceous components, the nature of the particular high surface area, porous glass material used, and the like. Recognizing that loading levels can vary widely as a result of the above factors, the values presented in Table I for each of the contacting steps of the present invention are provided merely to provide guidance to those of skill in the art.

TABLE I

|  | Loading Levels, mg TNF/mL Contacting Material | | |
|---|---|---|---|
|  | Broad | Preferred | Most Preferred |
| First Step* | <10 | 1–4 | ~2 |
| Second Step** | <6 | 1–4 | ~2 |
| Third Step*** | <10 | 2–8 | 4–5 |

*First contacting step employs high surface area, porous glass bead material
**Second contacting step employs a strong anion exchange resin
***Third contacting step employs an immobilized dye affinity material The recommended loading levels set forth in Table I can be achieved by adjusting either the quantity of broth which is contacted with a given contacting material at a given time or by adjusting the quantity of contacting material used for a given volume (and concentration) of broth. Since each of the contacting materials used in the various stages of my invention TNF purification procedure generally has different loading capacities, it is sometimes necessary to vary the amount of contacting material used at each stage of the purification sequence.

The TNF-containing fermentation broth applied to the high surface area, porous glass material can be disrupted and clarified employing techniques known by those of skill in the art, such as for example, pressure disruption, vigorous stirring in the presence of glass beads, enzymatic digestion of cell walls, e.g. with Zymolyase, chemical disruption, e.g., with methylene chloride, and the like. Preferably, disruption of the cells will be carried out at a pH sufficiently high so as to provide a post-disruption pH in the range of about 6 up to 8, so as to provide a medium in which the desired TNF remains in a stable form.

Once disrupted, the cell debris is removed from the broth containing the disrupted cells employed techniques known by those of skill in the art. For example, techniques which can be employed for the preparation of clarified, cell-free fermentation broth include centrifugation, microfiltration, and the like.

Once the disrupted, clarified fermentation broth has been applied to the high surface area, porous glass material, the glass material is then washed with at least three volumes (volumes of wash solution per volume of glass material) of a suitable buffer in order to remove those components of the broth which do not adhere to the high surface area, porous glass material employed in the first contacting step. Up to ten or more volumes of buffer can be employed for such washing. The upper limit as to the appropriate amount of washing is more a functon of convenience and practical considerations such as the cost of added buffer, the added time required for additional washing, the increased quantity of effluent to be disposed of, and the like. Those of skill in the art can readily determine the nature of suitable buffers employed for such purpose. Typically, I have employed a buffer comprising 0.01M potassium phosphate at a pH of about 7.5 for this washing step, although any buffer capable of maintaining a pH in the range of about 6.5 up to 7.5 or so is suitable for the washing step. Buffers having a concentration in the range of about 0.002 up to 0.1M are suitable for this purpose.

Once the high surface area, porous glass material has been sufficiently washed, a TNF-containing fraction is eluted therefrom with a solution comprising in the range of about 0.01 up to 10 V/V percent of a suitable eluant which is capable of causing desorption of TNF from the high surface area, porous glass material, but which does not significantly interfere with the binding of the TNF to the anion exchange resin employed in the second contacting step. Such eluants typically are compounds which impart a basic pH to the eluting solution and/or contain at least one hydroxyl group. Exemplary eluants include:

(a) compounds of the formula:

$$CR_2X(CRX)_nCR_2X$$

wherein n=0, 1, or 2; each R is independently H or methyl and X is hydroxyl or R, with the proviso that at least one X is hydroxyl;

(b) compounds of the formula:

$$NR'_xH_{3-x}$$

wherein x=1, 2 or 3; and each R' is independently a $C_1$ up to $C_6$ alkyl or cycloalkyl radical, said R' optically containing one or more hydroxyl substituents; and (c) combinations of compounds capable of providing a buffered solution with a pH in the range of about 8 up to 11, such as for example, carbonates, phosphates, borates, and the like.

Exemplary compounds which satisfy the above formulae include ethylene glycol, glycerol, propylene glycol, ethylamine, propylamine, butylamine, triethylamine, ethanolamine, triethanolamine, and the like, as well as mixtures of any two or more thereof.

When carried out in the preferred column configuration mode, the effluent of the first column containing high surface area, porous glass packing material is monitored by suitable means for the presence of protein. Suitable means for such purpose can readily be determined by those of skill in the art. For example, monitoring of the ultraviolet (uv) absorption at 280 nm is convenient. Once such monitoring reveals that protein is beginning to elute from the first column, the effluent from the first column is then fed directly into a second column comprising an anion exchange resin. Such introduction of the effluent from the first column is continued until monitoring of the effluent from the first column reveals that no more protein is being eluted from the first column.

In accordance with this preferred embodiment of the present invention, the protein-containing fraction from the first column is introduced directly into the second column, thereby minimizing the amount of sample handling to which the TNF-containing samples are subjected and avoiding the need to carry out any sample modification before additional purification can be accomplished.

Anion exchange resins contemplated for use in the practice of the present invention are strong anion exchangers, such as, for example, quaternary ammonium anion exchange resins. Such resins can be prepared on a variety of supports, e.g., silica, cellulose, polystyrene, and the like.

As recognized by those of skill in the art, the anion exchange resin is typically equilibrated with suitable buffer prior to loading with TNF-containing fluid. I have found a buffer comprising 0.02M Tris-HCl, pH 8.3 to be convenient and effective, although any buffer capable of maintaining a pH in the range of about 7.8 up to 10 is suitable. Buffers employed typically have a concentration in the range of about 0.002 up to 0.1M.

After the TNF-containing effluent from the high surface area, porous glass material has been contacted with the anion exchange resin, yet before elution of the TNF from the anion exchange resin, the TNF-loaded resin is washed with additional volumes of the same buffer used to equilibrate the resin before it was loaded with TNF-containing fluid. In the range of 1–2 volumes of more of buffer (volumes of wash buffer per volume of anion exchange resin) are employed. The minimum amount required is that amount which will return the pH of the effluent from the anion exchange resin to approximately the pH of the resin before the TNF-containing solution was loaded thereon. The upper limit as to the amount of buffer to employ for this washing-/equilibration step is mainly a matter of convenience. In a presently preferred embodiment of the invention, the anion exchange resin is equilibrated to a pH of about 8.3 prior to eluting the TNF-containing fraction therefrom by passing therethrough additional quantities of 0.02M Tris-HCl buffer, pH 8.3, although any buffer capable of maintaining a pH in the range of about 7.8 up to 10 is suitable. Buffers employed typically have a concentration in the range of about 0.002 up to 0.1M.

When carried out in the preferred column configuration, the second column containing the anion exchange resin is loaded with TNF-containing effluent from the first column (containing the high surface area, porous glass packing), and then washed. A TNF-containing fracton is then eluted from the second column with a solution comprising at least about 0.2M concentration of a soluble metal salt in a suitable buffer. Suitable soluble salts include salts of the anions: halides, phosphates, sulfates, acetates, nitrates, and the like. Sodium chloride is presently preferred because it is inexpensive and readily available. Suitable buffers are those which are capable of maintaining the pH of the eluting solution in the range of about 7.8 up to 10. Salt concentrations in the range of about 0.1 up to 0.5M are suitable, with the higher concentrations generally causing TNF to more readily elute from the second column. In general, higher salt concentrations are required for TNF to elute at higher pH values, while lower salt concentrations are suitable for TNF elution at lower pH values. In practice, I prefer to employ a solution comprising sodium chloride in 0.01M Tris-HCl buffer, pH 8.3. This elution can be carried out in a variety of ways, such as, for example, employing a linear gradient of low (e.g., 0.1M) to high (e.g., 0.3M) sodium chloride content eluent, or a stepwise gradient from no sodium chloride to a high (e.g., 0.2M) sodium chloride containing eluant.

When carried out in the preferred column configuration, the effluent from the second column can conveniently be monitored for the elution of protein-containing fluid by suitable means, such as for example, monitoring the uv absorbance at about 280 nm. Once protein-containing fluid begins to elute from the second column, this effluent can then be passed directly into a third column comprising an immobilized dye affinity chromatography column.

By directly introducing the protein-containing effluent from the second column into the third column, the need to carry out any sample modification such as concentration, reformulation, etc. is avoided.

The term "immobilized dye affinity chromatography column" as used in this specification refers to a variant of affinity chromatography in which synthetic triazine dyes are used in place of the natural substrates, cofactors or effectors commonly employed as immobilized ligands. Those of skill in the art are well aware of numerous dye ligands which are suitable in the practice of the present invention. Exemplary ligands include the Red, Orange, Green and Blue dyes, whose ligand moieties are depicted below:

Blue dye

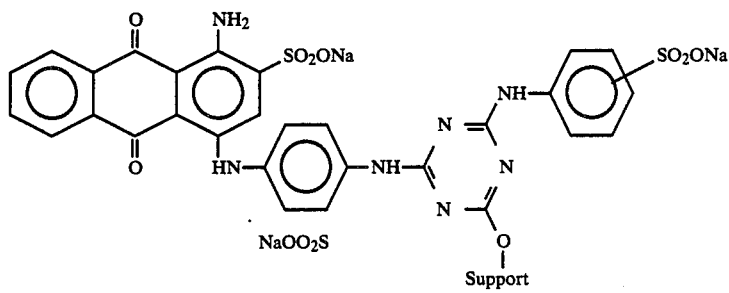

Red dye

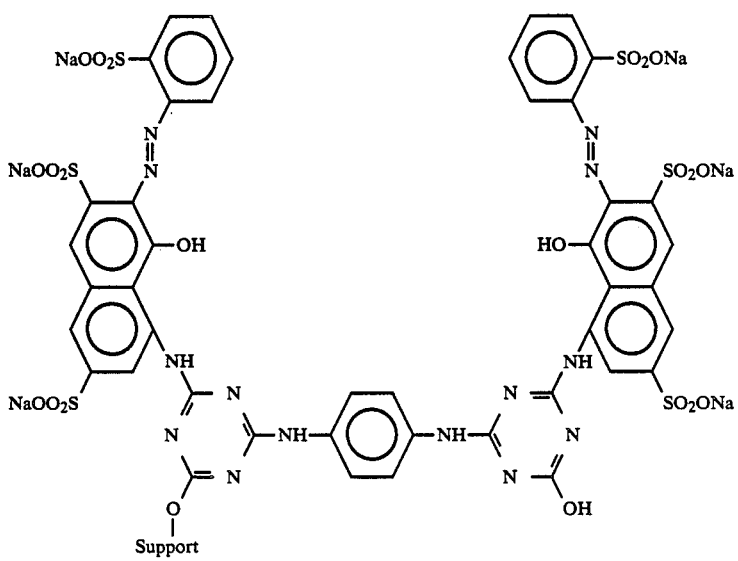

Orange dye

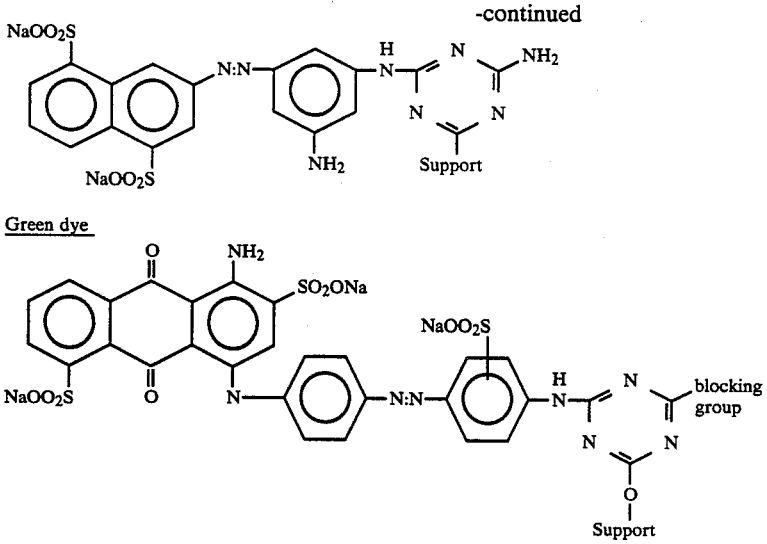

Green dye

These ligand moieties can be immobilized on a wide variety of supports, such as, for example, silica, glass, cellulose, Sepharose, Sephadex, and the like. The Blue A dye ligand has been found to provide excellent results and therefore is the presently preferred ligand (on a solid support) as the contacting material for the third contacting step employed in the invention TNF purification procedure.

Those of skill in the art recognize that the immobilized dye affinity material employed in the practice of the present invention will generally be equilibrated with suitable buffer prior to loading the effluent of the anion exchange resin thereon. In practice, I have found equilibration of the immobilized dye affinity material with a buffer comprising 0.02M Tris-HCl, pH 8.3, to be useful for this purpose, although any buffer capable of maintaining a pH in the range of about 6.0 up to 8.5 is suitable. Buffers employed typically have a concentration in the range of about 0.002 up to 0.1M.

When carried out in the preferred column configuration mode, substantially all of the protein-containing material eluted from the second column (containing anion exchange resin packing) is loaded onto the third column, which is packed with immobilized dye affinity material. The third column is then washed with sufficient quantitites of a suitable buffer until essentially no material having a uv absorbance in the range of about 280 nm is eluted. A buffer system I have found useful for this purpose comprises 0.02M Tris-HCl, pH 8.3, although those of skilled in the art recognize that other buffer systems are suitable for washing of the third column prior to elution of the TNF therefrom, such as for example, buffers capable of maintaining a pH in the range of about 6.0 up to 8.5. Buffers employed typically have a concentration in the range of about 0.002 up to 0.1M.

Once all of the 280 nm absorbing material has been washed from the loaded third column, TNF-containing fluid is eluted from the column with an eluant comprising a suitable buffer, optionally having a high salt concentration. Exemplary salts include soluble salts of the anions: halides, phosphates, sulfates, acetates, nitrates, thiocyanates, and the like. Those of skill in the art can readily determine suitable salt concentrations to employ for such elution, depending on such factors as the size of column employed, the quantity of TNF absorbed on the column, and the like. Salt concentrations in the range of about 0.3 up to 1M and higher are suitable for elution of TNF. The salts employed are dissolved in a suitable buffer, such that the resulting solution causes desorption of TNF from the third column without causing the degradation of the TNF. Thus, buffers in the pH range of about 6.5 up to 10 are suitable. At the high pH extreme, little, if any, added salt is required to cause elution of the TNF. Optionally, added reagents which promote desorption of TNF from the third column can also be included in the eluting solution, such as, for example, non-ionic detergents. In practice, I have found an eluant composition comprising about 1.0M sodium chloride in a 0.02M Tris-HCl buffer at pH of 8.3 to be suitable.

The effluent from the third column is monitored by suitable means to identify the protein-containing fractions, which can then be pooled and subjected to further treatment to remove undesired salts therefrom and to further concentrate the TNF-containing fraction. Such well known techniques as dialysis, vacuum dialysis, ultrafiltration, lyophilization, and the like can be employed.

A further understanding of the present invention and its advantages will be provided by reference to the following non-limiting examples.

EXAMPLE I

Production of TNF-Containing Broth

A strain of *Pichia pastoris* containing an integrated, methanol-responsive TNF-encoding expression cassette, and designated GTS115/pTNF6-5 (available from the Northern Regional Research Center of the US Department of Agriculture, Peoria, Ill., with the accession number NRRL Y-18116) was grown on 20% w/v glycerol to a steady-state growth yield of 108 g/L dry cell weight. After a 30-minute starvation period, 20 mL of methanol was added to the 200 mL culture. An immediate decrease in both D.O. and pH was noted. A total of 275 mL (217 g) of methanol was added to the culture over a period of 189 hours. Nineteen methanol additions were required over the time period. Nearly all of the methanol was oxidized.

The production of TNF in GTS115/pTNF6-5 cells was rapidly induced upon shifting to methanol and appeared to reach saturation values of greater than 100×10⁴ within 48 hours. The TNF level continued to be steady until the end of the run, which was carried out for about 189 hours.

EXAMPLE II

Pichia broth at ~100 g/L was prepared as described in Example I, and frozen at −20° until use. About 100 mL of thawed cell broth was adjusted to pH 8 with 0.1N NaOH, disrupted by agitation with glass beads in a water-jacketted blender for 3 to 5 minutes, and clarified by centrifugation at 30,000×G for 15 minutes. The supernatant was applied directly to a column containing 60 mL of controlled pore glass (CPG; surface area=36.4 m²/g, mean pore volume=654 Angstroms, pore volume=0.91 cc/g). The bulk of the Pichia proteins eluted with about five column volumes of 0.01M potassium phosphate (pH 7.5). TNF was then eluted with 5% aqueous triethanolamine. As the protein peak emerged from the CPG column, the CPG column outlet was connected to the inlet of an Accell QA anion exchange column containing 60 mL of resin (37–55 micron particles of non-compressible silica, 500 Angstrom pore size, with quaternary methyl amine ion exchange facility bonded thereto). Subsequently, the CPG column was disconnected and TNF eluted from the anion exchange column with a sufficient quantity of 0.2M NaCl in 0.02M Tris-HCl (pH 8.3) to elute the TNF-containing protein peak.

As the protein peak emerged from the anion exchange column, the anion exchange column outlet was connected to the inlet of a Blue A Dye column containing 20 mL of packing (Blue dye linked to a cross-linked 5% agarose support matrix via an ether linkage to the triazine ring of the dye); followed by washing with about 4 column volumes of a buffer comprising 0.02M Tris-HCl (pH 8.3), i.e., until all of the 280 nm material was eluted, and finally eluting the purified TNF with a solution comprising 1.0M NaCl in 0.02M Tris-HCl (pH 8.3).

The specific activity (U/mg) of a representative purified TNF obtained from *P. pastoris* was determined to be 2.6×10⁷ for frozen sample and 3.0×10⁷ for freeze dried sample.

The yield of TNF was 78% based on the number of Units of TNF initially loaded onto the first column. The purity of TNF obtained as a result of the invention procedure was determined to be about 98% by Coomassie Brilliant Blue R stained SDS-PAGE gel. All the purification steps were completed within 24 hours.

The examples have been provided merely to illustrate the practice of my invention and should not be read so as to limit the scope of my invention or the appended claims in any way. Reasonable variations and modifications, not departing from the essence and spirit of my invention, are contemplated to be within the scope of patent protection desired and sought.

That which is claimed is:

1. A method for the purification of recombinant tumor necrosis factor, TNF, from clarified, disrupted yeast fermentation broth containing same which comprises:
(a) applying said broth to porous glass beads composed of porous granules of high silica glass permeated by interconnecting pores of uniform size in the range of about 300 up to 3000 Angstroms;
(b) washing the porous glass beads loaded with said broth with a buffer to remove those components of the broth which do not adhere to said porous glass beads and to maintain a pH in the range of about 6.5 up to 7.5;
(c) eluting a first TNF-containing fraction from said porous glass beads with a solution comprising in the range of about 0.01 up to 10 V/V% of eluant which is capable of causing desorption of TNF from said porous glass beads but which does not significantly interfere with binding of TNF onto the anion exchange resin employed in step (d) which is at least one selected from the groups consisting of:
(i) compounds of the formula:

$$CR_2X(CRX)_nCR_2X$$

wherein n=0, 1, or 2; each R is independently H or methyl and X is hydroxyl or R, with the proviso that at least one X is hydroxyl;
(ii) compounds of the formula:

$$NR'_xH_{3-x}$$

wherein x=1, 2, or 3, and each R' is independently selected from a $C_1$ up to $C_6$ alkyl or cycloalkyl radical, wherein each R' optionally contains one or more hydroxyl groups; and
(iii) combinations of compounds capable of providing a buffered solution with a pH in the range of about 8 up to 11;
(d) contacting said first TNF-containing fraction obtained from step (c) with quaternary ammonium anion exchange resin;
(e) eluting a second TNF-containing fraction from said anion exchange resin with a solution wherein the salt concentration which comprises at least about 0.2M concentration of a soluble salt selected from salts of:
halides,
phosphates,
sulfates,
acetates, and
nitrates;
in a buffer having a pH in the range of about 7.8 up to 10;
(f) contacting said second TNF-containing fraction from said anion exchange resin with an immobilized dye affinity material which comprises a dye of a support, wherein the dye is selected from the group consisting of
Red dye
Orange dye
Green dye and
Blue dye;
(g) washing said immobilized dye affinity material with a buffer having a pH in the range of about 7.8 up to 10 until essentially no material with a uv absorbance of about 280 nm is eluted, and thereafter
(h) eluting purified TNF from said immobilized dye affinity material with an eluant which comprises a concentration of at least 0.3M of a salt selected from the group consisting of soluble salts of the anions:
halides,
phosphates,
sulfates,
acetates,
nitrate, and
thiocyanates.

2. A method in accordance with claim 1 wherein said yeast fermentation broth is a broth containing cells of the species *Pichia pastoris*.

3. A method in accordance with claim 2 wherein said species of *Pichia pastoris* is *Pichia pastoris* GTS115-pTNF6-5 NRRL Y-18116.

4. A method in accordance with claim 1 wherein said porous glass beads, said anion exchange resin and said immobilized dye affinity material are contained in a first, second and third column, respectively.

5. A method in accordance with claim 4 further comprising equilibrating said first column prior to step (a).

6. A method in accordance with claim 4 further comprising equilibrating said second column prior to step (d) with a buffer capable of maintaining a pH in the range of about 7.8 up to 10.

7. A method in accordance with claim 4 further comprising equilibrating said second column to pH in the range of about 7.8 up to 10 prior to step (e) eluting of said TNF-containing fraction from said second column by passing there-through additional buffer having a pH in the range of 7.8 up to 10.

8. A method in accordance with claim 4 further comprising equilibrating said third column prior to step (f) with a buffer having a pH in the range of about 7.8 up to 10.

9. A method in accordance with claim 1 wherein said clarified, disrupted yeast fermentation broth is prepared by:
(i) disrupting the cells of the fermentation broth which has been adjusted to a pH to provide a post-disruption pH in the range of about 6 up to 8; and
(ii) clarifying the disrupted cells.

10. A method in accordance with claim 1 wherein said buffer of step (b) comprises 0.01M potassium phosphate, pH 7.5.

11. A method in accordance with claim 6 wherein a buffer comprising 0.02M Tris-HCl, pH 8.3 is employed for said equilibrating.

12. A method in accordance with claim 8 wherein a buffer comprising 0.02M Tris-HCl, pH 8.3 is employed for said equilibrating.

13. A method in accordance with claim 1 wherein said buffer of step (g) comprises 0.02M Tris-HCl, pH 8.3.

14. A method in accordance with claim 1 wherein said eluant is at least one selected from the group consisting of:
ethylene glycol,
glycerol,
propylene glycol,
ethylamine,
propylamine,
butylamine,
triethylamine,
ethanolamine, and
triethanolamine.

15. A method in accordance with claim 4 wherein the TNF-containing fraction from said first column is fed directly into the second column when monitoring of the effluent from the first column reveals the presence of protein therein; and wherein the TNF-containing fraction from said second column is fed directly into the third column when monitoring of the effluent from the second column reveals the presence of protein therein.

16. A method for the purification of recombinant tumor necrosis factor, TNF, from disrupted, clarified fermentation broth which comprises:
(a) applying the disrupted, clarified fermentation broth to a first column containing high surface area, porous glass bead packing;
(b) washing the first column loaded in accordance with step (a) with at least three column volumes of a buffer comprising 0.01M potassium phosphate at a pH of about 7.5;
(c) eluting a first TNF-containing fraction from said first column with a solution comprising in the range of about 0.01 up to 10 V/V% of triethanolamine;
(d) passing the TNF-containing fraction from said first column into a second column comprising an anion exchange resin when monitoring of the second effluent from the first column reveals that said effluent contains protein;
(e) equilibrating said second column to pH 8.3 by passing therethrough with at least one column volume of pH 8.3 0.02M Tris-HCl buffer;
(f) eluting a second TNF-containing fraction from said second column with a solution comprising 0.1 up to 0.3M NaCl in 0.01M Tris-HCl pH 8.3 buffer;
(g) passing the TNF-containing fraction from said second column into a third column comprising an immobilized dye affinity chromatography column when monitoring of the effluent from the second column reveals that said effluent contains protein;
(h) washing said third column with a suitable buffer until essentially no material with a UV absorbance of about 280 nm is eluted, and
(i) eluting purified TNF with an eluant comprising 1.0M NaCl in a 0.02M Tris-HCl buffer, pH 8.3.

* * * * *